United States Patent [19]

Kiener et al.

[11] Patent Number: 5,266,482
[45] Date of Patent: Nov. 30, 1993

[54] AGROBACTERIUM USEFUL FOR THE MICROBIOLOGICAL PROCESS FOR THE PRODUCTION OF HYDROXYLATED PYRAZINE DERIVATIVES

[75] Inventors: Andreas Kiener, Visp; Klaus Heinzmann, Visperterminen; Michael Bokel, Visp, all of Switzerland

[73] Assignee: Lonza Ltd., Gampel/Valais, Switzerland

[21] Appl. No.: 888,659

[22] Filed: May 27, 1992

Related U.S. Application Data

[62] Division of Ser. No. 788,375, Nov. 6, 1991, Pat. No. 5,173,412.

[30] Foreign Application Priority Data

Nov. 8, 1990 [CH] Switzerland .................. 3550/90

[51] Int. Cl.$^5$ .................. C12R 1/01; C12P 17/12
[52] U.S. Cl. .................. 435/252.2; 435/122; 435/822
[58] Field of Search .................. 435/252.2, 822, 122

[56] References Cited

U.S. PATENT DOCUMENTS

| 4,011,135 | 3/1977 | Kamatani et al. .................. 435/822 |
| 4,259,451 | 3/1981 | Steenbergen et al. .................. 435/822 |
| 4,321,326 | 3/1982 | Sykes et al. .................. 435/822 |
| 4,657,140 | 1/1986 | Voelskow et al. .................. 435/822 |
| 4,689,160 | 8/1987 | Steenbergen et al. .................. 435/822 |
| 5,173,412 | 12/1992 | Kiener et al. .................. 435/822 |

FOREIGN PATENT DOCUMENTS 0434035 6/1991 European Pat. Off. .................. 435/122

OTHER PUBLICATIONS

Maga and Sizer, J. Agric. Food Chem., 21 (1973), pp. 22 to 30.
Karmas and Spoerri, J. Amer. Chem. Soc., 74 (1952), pp. 1580 to 1584.
MacDonald, J. C., Bishop, G. C., Mazurek, Tetrahedron 32, (1976) pp. 655 to 660.
Drews, G., Mikrobiologisches Praktikum, 4th Ed., Springer Verlag, (1983), pp. 1 to 85.

*Primary Examiner*—Herbert J. Lilling
*Attorney, Agent, or Firm*—Fisher, Christen & Sabol

[57] ABSTRACT

Microorganisms, which are capable of growing with pyrazine as the sole carbon, nitrogen and energy source. These microorganisms hydroxylate pyrazine derivatives of general formula:

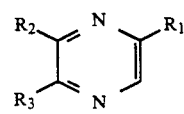

I to hydroxylated pyrazine derivatives of general formula:

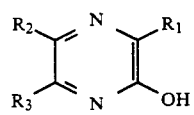

II and the latter are accumulated in the growth medium.

3 Claims, No Drawings

AGROBACTERIUM USEFUL FOR THE MICROBIOLOGICAL PROCESS FOR THE PRODUCTION OF HYDROXYLATED PYRAZINE DERIVATIVES

This is a divisional of application Ser. No. 788,375, filed on Nov. 6, 1991 now U.S. Pat. No. 5,173,412, of Andreas KIENER et al., for MICROBIOLOGICAL PROCESS FOR THE PRODUCTION OF HYDROXYLATED PYRAZINE DERIVATIVES.

BACKGROUND OF THE INVENTION

1. Field of the Invention

The invention relates to new microorganisms, which grow with pyrazine, and hydroxylate pyrazine derivatives of the general formula:

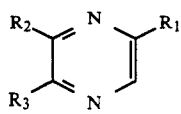

wherein $R_1$ means a hydrogen atom or a halogen atom and $R_2$ and $R_3$ are the same or different and mean a hydrogen atom or a $C_1$–$C_4$ alkyl group, but $R_1$, $R_2$ and $R_3$ do not all simultaneously mean hydrogen, as well as to a process for the production of hydroxylated pyrazine derivatives.

2. Background Art

Hydroxylated pyrazine derivatives are, for example, important intermediate products for the production of methoxyalkylpyrazines. Methoxyalkylpyrazines are essential components of aromatic substances [Maga and Sizer. J. Agric., Food Chem., 21, (1973), pages 22 to 30].

So far, only chemical processes for the production of hydroxylated pyrazines have been known, such as, the one described by *Karmas and Spoerri*, in J. Amer. Chem. Soc., 74, (1952), pages 1580 to 1584, in which, for example, 2-hydroxy-5-methylpyrazine is synthesized starting from methylglyoxal and glycinamide hydrochloride. But this process has the drawback that the product is greatly contaminated.

In addition, studies on the biological catabolism of 2-hydroxypyrazine are described in *Matley and Harle*, Biochem. Soc. Trans., 4, (1976), pages 492 to 493.

A biotechnological process for the production of regiospecific hydroxylated pyrazine derivatives, starting from substituted pyrazine derivatives with microorganisms, which grow with pyrazine, is not known.

BROAD DESCRIPTION OF THE INVENTION

The main object of the invention is to provide new microorganisms, which regiospecifically hydroxylate pyrazine derivatives of general formula I economically in a biotechnological way and in a simple way, as well as to provide a biotechnological process for the production of hydroxylated pyrazine derivatives. Other objects and advantages of the invention are set out herein or are obvious herefrom to one skilled in the art.

The objects and advantages of the invention are achieved by the microorganisms of the invention and the processes of the invention. The microorganisms of the invention are capable or growing with pyrazine as the sole carbon, nitrogen and energy source and as substrate react pyrazine derivatives of the general formula:

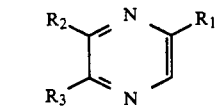

wherein $R_1$ is a hydrogen atom or a halogen atom and $R_2$ and $R_3$ are the same or different and are each a hydrogen atom or a $C_1$–$C_4$ alkyl group, but $R_1$, $R_2$ and $R_3$ are not all simultaneously hydrogen, to a hydroxylated pyrazine derivative of the general formula:

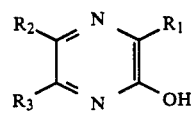

wherein $R_1$, $R_2$ and $R_3$ have the above-mentioned meaning, and the latter is accumulated in the growth medium. The invention includes the microorganisms of the invention in the form of biologically pure or substantially biologically pure cultures thereof.

A preferred microorganism according to the invention is the microorganism with the designation Agrobacterium sp. deposited in the DSM with the number 6136. The invention includes its descendants and mutants.

The invention includes a process for the production of hydroxylated pyrazine derivatives using one of the invention microorganisms to convert a pyrazine derivative of the general formula:

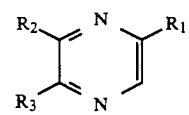

wherein $R_1$ is a hydrogen atom or a halogen atom and $R_2$ and $R_3$ are the same or different and are each a hydrogen atom or a $C_1$–$C_4$ alkyl group, but $R_1$, $R_2$ and $R_3$ are not all simultaneously hydrogen, to a hydroxylated pyrazine derivative of the general formula:

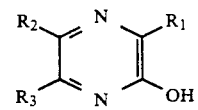

wherein $R_1$, $R_2$ and $R_3$ have the above-mentioned meaning, and the concentrated product is isolated.

Preferably the active enzymes of the microorganism are induced with pyrazine. Preferably the reaction is performed with one-time or continuous addition of the substrate, so that the substrate concentration in the culture medium does not exceed 20 percent (w/v). Preferably the reaction is performed at a pH of 4 to 10. Also, preferably, the reaction is performed at temperatures of 0° to 55° C.

The invention also includes the compound 6-Ethyl-2-hydroxypyrazine.

DETAILED DESCRIPTION OF THE INVENTION

According to the invention, all microorganisms are suitable which use pyrazine as the sole carbon, nitrogen and energy sources and are selected according to usual microbiological techniques, e.g., from soil samples, sewage treatment plants, earth, anthills and compost piles. Suitably, all gram-positive and gram-negative microorganisms can be used which catabolize pyrazine and hydroxylate a pyrazine derivative of general formula I as a substrate in a hydroxylated pyrazine derivative of general formula II and accumulate the latter in the growth medium.

A preferred microorganism is Agrobacterium radiobacter DRS 3 with DSM (German Collection of Microorganisms) no. 6136, which is designated below, because of detailed identification data, as microorganism Agrobacterium sp. (DSM no. 6136). This strain was deposited on Sep. 7, 1990 in the German Collection of Microorganisms (DSM) and Zellkulturen [Cell Cultures] GmbH, Mascherodeweg 1b, 3300 Brunswick/FRG.

| Scientific description of Agrobacterium sp. (DSM no. 6136) | | | |
|---|---|---|---|
| cell shape | rods | ADH | − |
| width micron | 0.6–0.8 | LDC | − |
| length micron | 1.5–3.0 | ODC | − |
| mobility | + | ONPG | + |
| gram-reaction | − | VP | − |
| lysis by 3% KOH | + | indole | − |
| aminopeptidase (Cerny) | + | NO$_2$ from NO$_3$ | + |
| spores | − | denitrification | + |
| oxidase | + | phenylalanine- | − |
| catalase | W | desaminase | |
| growth | | lecithinase | − |
| anaerobic | − | urease | + |
| 37/41° C. | −/− | Simmons citrate | − |
| pH 5.6 | − | malonate | − |
| Mac-Conkey-Agar | + | ketolactose | − |
| SS-Agar | − | hydrolysis of | |
| cetrimide agar | − | starch | − |
| 2% NaCl | − | gelatin | − |
| pigments | | casein | − |
| nondiffusing | − | DNA | − |
| diffusing | − | Tween 80 | − |
| fluorescing | − | Aesculin | + |
| pyocyanin | − | tyrosine | − |
| acid from (OF test) | | catabolism | |
| aerobic glucose | − | alkalization of | + |
| anaerobic glucose | − | litmus milk | |
| gas from glucose | − | growth substance | − |
| acid from (ASS) | | requirement | |
| glucose | + | substrate utilization | |
| fructose | + | acetate | + |
| xylose | + | adipate | − |
| ethanol | + | caprate | − |
| m-erylthritol | + | citrate | − |
| melezitose | − | glycolate | + |
| arabinose | + | lactate | + |
| saccharose | + | laevulinat | − |
| cellobiose | + | malate | + |
| trehalose | + | | |
| rhamnose | + | | |
| dulcitol | − | | |
| sorbitol | + | | |
| glycerol | + | | |
| malonate | − | | |
| phenyl acetate | − | | |
| suberate | − | | |
| sebacinate | − | | |
| m-tartrate | − | | |
| L-arabinose | + | | |
| fructose | + | | |
| glucose | + | | |
| mannose | + | | |
| maltose | + | | |
| xylose | + | | |
| fucose | − | | |
| mannitol | + | | |
| 2-ketogluconate | − | | |
| N-acetylglocosamine | + | | |

| -continued | |
|---|---|
| Scientific description of Agrobacterium sp. (DSM no. 6136) | |
| L-asparate | + |
| L-serine | + |
| L-glutamate | + |
| L-histidine | − |
| hydroxybutyrate | − |
| betaine | + |
| methylamine | − |
| methanol | − |
| ethanol | − |
| Main quinone component: ubiquinone 10 | |

For the process for the production of hydroxylated pyrazine derivatives a pyrazine derivate of the general formula I as substrate:

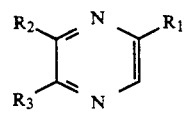

wherein R$_1$ is a hydrogen atom or a hydrogen atom and R$_2$ and R$_3$ are the same or different and are a hydrogen atom or a C$_1$–C$_4$ alkyl group, but R$_1$, R$_2$ and R$_3$ are not all simultaneously hydrogen is converted with the microorganisms set out above to a hydroxylated pyrazine derivative of general formula II:

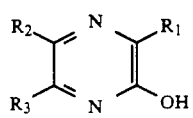

in which R$_1$, R$_2$ and R$_3$ have the above-mentioned meaning, and the concentrated product is isolated. Preferably, hydroxylated pyrazine derivatives are produced by these microorganisms, wherein R$_1$ means a hydrogen atom or a chlorine atom and R$_2$ and R$_3$ are the same or different and are a hydrogen atom, a methyl group or ethyl group, but R$_1$, R$_2$ and R$_3$ are not all simultaneously hydrogen.

Also, a new hydroxylated pyrazine derivative, 6-ethyl-2-hydroxypyrazine, was produced by these microorganisms.

Usually, the microorganisms are cultivated before the actual process (substrate reaction) in a medium containing a growth substrate. The growth substrate pyrazine is used in an amount of 0.001 to 10 percent by weight, relative to the culture medium, preferably in an amount of 0.001 to 5 percent by weight, relative to the culture medium.

The enzymes of the microorganism responsible for hydroxylation are suitably induced by pyrazine. The compound used for induction either can be present during the reaction of the pyrazine derivative (substrate) or the feed of this induction compound can be stopped during the reaction. Preferably, the feed of the compounds used for induction is stopped during the reaction of the pyrazine derivative either by stopping the feed o by centrifuging the cells.

Before adding the substrate, the cells are cultivated up to an optical density of 100 at 650 nm, preferably up to an optical density of 10 to 60 at 650 nm.

As a nutrient medium for the microorganisms, both for the cultivation and for the actual process, the media usual among experts can be used. Preferably, the medium is used whose composition is indicated in Table 1 below.

Usually, the actual process is then performed with dormant cells.

The pyrazine derivative of general formula I can be fed as a substrate one-time or continuously to the cell suspension, preferably so that the substrate concentration in the culture medium does not exceed 20 percent (w/v). In particular, the substrate concentration does not exceed 5 percent (w/v) in the culture medium.

The reaction is suitably performed in a pH range of 4 to 10, preferably 6 to 8. Usually the reaction is performed at a temperature of 0° to 55° C., preferably at 20° to 40° C.

After a usual reaction time of 5 to 100 hours, the hydroxylated pyrazine derivatives can be isolated in the known way, for example, by extraction with a suitable organic solvent. Suitably, the hydroxylated pyrazine derivatives are isolated by extraction with chlorinated organic solvents, such as, chlorinated hydrocarbons or ethyl acetate.

EXAMPLE 1

Isolation of Pyrazine-Metabolizing Microorganisms

Aerobic pyrazine-metabolizing microorganisms were concentrated in the A+N medium (Table 1) with the adding of 0.1 percent (w/v) of pyrazine as the sole carbon and energy source. The general techniques for isolating microorganisms are described, for example, in G. Drews, Mikrobiologisches Praktikum [Microbiological Workshop], 4th ed., Springer Verlag, (1983).

As an inoculum, samples from the earth, sewage treatment plants, compost and anthills were used. The concentrations were cultivated in shaking flasks at 30° C. After inoculating three times in fresh medium, the concentrations of the same medium were streaked by adding 16 g of agar per liter and were incubated at 30° C. After repeated streaking on agar medium, pure cultures were able to be isolated.

TABLE 1

| A + N Medium | |
|---|---|
| Composition: | Concentration (mg/l) |
| $(NH_4)_2SO_4$ | 2000 |
| $Na_2HPO_4$ | 2000 |
| $KH_2PO_4$ | 1000 |
| NaCl | 3000 |
| $MgCl_2.6H_2O$ | 400 |
| $CaCl_2.2H_2O$ | 14.5 |
| $FeCl_3.6H_2O$ | 0.8 |
| pyridoxal-hydrochloride | $10 \cdot 10^{-3}$ |
| riboflavin | $5 \cdot 10^{-3}$ |
| nicotinic acid amide | $5 \cdot 10^{-3}$ |
| thiamin hydrochloride | $2 \cdot 10^{-3}$ |
| biotin | $2 \cdot 10^{-3}$ |
| pantothenic acid | $5 \cdot 10^{-3}$ |
| p-aminobenzoate | $5 \cdot 10^{-3}$ |
| folic acid | $2 \cdot 10^{-3}$ |
| vitamin B12 | $5 \cdot 10^{-3}$ |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $200 \cdot 10^{-3}$ |
| $CuCl_2.2H_2O$ | $10 \cdot 10^{-3}$ |
| $NiCl_2.6H_2O$ | $20 \cdot 10^{-3}$ |
| $Na_2MoO_4.2H_2O$ | $30 \cdot 10^{-3}$ |
| $EDTANa_2.2H_2O$ | $5 \cdot 10^{-3}$ |
| $FeSO_4.7H_2O$ | $2 \cdot 10^{-3}$ |
| (pH of the solution was adjusted to 7.0) | |

EXAMPLE 2

Reaction of 3-chloropyrazine to 3-chloro-2-hydroxypyrazine Agrobacterium sp.

Agrobacterium sp. DSM no. 6136 was cultivated in the A+N medium with 0.1 percent (w/v) of pyrazine in a fermenter at pH 7 and a temperature of 30° C. Then, the cells were centrifuged, resuspended again in the A+N medium and adjusted to an optical density of 10 at 650 nm. This cell suspension was added in a shaking flask and mixed with 26 mmol of 3-chloropyrazine per liter (0.3 percent w/v).

After an incubation of 8 hours at 30° C. in a shaking machine, 20 mmol of 3-chloro-2-hydroxypyrazine per liter, corresponding to a yield of 77 percent, was detected.

EXAMPLES 3 TO 5

Examples 3 to 5 were performed corresponding to Example 2 and are summarized in Table 2. The position of the hydroxyl group was determined according to the data of MacDonald. J. C., Bishop, G. C., Mazurek, Tetrahedron, 32, (1976), p. 655 ff.

TABLE 2

| Ex. | Substrate | Conc. of the heterocycle in % (w/v) in the medium | Reaction time in hours | End product | Yield in % |
|---|---|---|---|---|---|
| 3 | 2-methylpyrazine | 0.2 | 1 | 2-hydroxy-6-methylpyrazine | 50 |
| 4 | 2-ethylpyrazine | 0.2 | 24 | 6-ethyl-2-hydroxypyrazine | 20 |
| 5 | 2,3-dimethylpyrazine | 0.2 | 10 | 2-hydroxy-5,6-dimethylpyrazine | 20 |

What is claimed is:

1. Biologically pure culture of Agrobacterium sp. deposited in the DSM with the number 6136, a descendant thereof or a mutant thereof, said descendant and said mutant each being capable of growing with pyrazine as sole carbon, nitrogen and energy source and convert as a substrate a pyrazine derivative of formula:

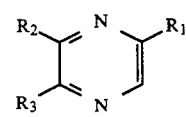

wherein $R_1$ is a hydrogen atom or a halogen atom and $R_2$ and $R_3$ are the same or different and are each a hydrogen atom or a $C_1$-$C_4$ alkyl group, but $R_1$, $R_2$ and $R_3$ are not all simultaneously hydrogen, to a hydroxylated pyrazine derivative of formula:

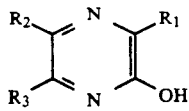

wherein $R_1$, $R_2$ and $R_3$ have the above-mentioned meaning, and the hydroxylated pyrazine derivative of formula II is accumulated in the growth medium.

2. The biologically pure culture according to claim 1 of Agrobacterium sp. DSM 6136.

3. Agrobacterium sp. deposited in the DSM with the number 6136, a descendant thereof or a mutant thereof, said descendant and said mutant each being capable of growing with pyrazine as sole carbon, nitrogen and energy source and converting as a substrate a pyrazine derivative of formula:

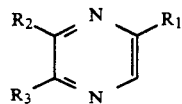

wherein $R_1$ is a hydrogen atom or a halogen atom and $R_2$ and $R_3$ are the same or different and are a hydrogen atom or a $C_1$–$C_4$ alkyl group, but $R_1$, $R_2$ and $R_3$ are not all simultaneously hydrogen, to a hydroxylated pyrazine derivative of formula:

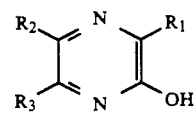

wherein $R_1$, $R_2$ and $R_3$ have the above-mentioned meaning, and the hydroxylated pyrazine derivative of formula II is accumulated in the growth medium, said Agrobacterium sp. DSM 6136, said descendant or said mutant each being in pure form.

* * * * *